US011292764B2

(12) United States Patent
Zhang et al.

(10) Patent No.: US 11,292,764 B2
(45) Date of Patent: Apr. 5, 2022

(54) CYCLIC SULFONATE COMPOUNDS AS PHOTOACID GENERATORS IN RESIST APPLICATIONS

(71) Applicant: HERAEUS EPURIO LLC, Vandalia, OH (US)

(72) Inventors: Yongqiang Zhang, Vandalia, OH (US); Ram B. Sharma, Vandalia, OH (US)

(73) Assignee: HERAEUS EPURIO LLC, Vandalia, OH (US)

( * ) Notice: Subject to any disclaimer, the term of this patent is extended or adjusted under 35 U.S.C. 154(b) by 349 days.

(21) Appl. No.: 16/495,719

(22) PCT Filed: Mar. 14, 2019

(86) PCT No.: PCT/US2019/022252
§ 371 (c)(1),
(2) Date: Sep. 19, 2019

(87) PCT Pub. No.: WO2019/178344
PCT Pub. Date: Sep. 19, 2019

(65) Prior Publication Data
US 2020/0017441 A1 Jan. 16, 2020
US 2021/0002213 A9 Jan. 7, 2021

Related U.S. Application Data

(60) Provisional application No. 62/644,288, filed on Mar. 16, 2018.

(51) Int. Cl.
C07C 309/10 (2006.01)
G03F 7/004 (2006.01)
C07C 381/12 (2006.01)

(52) U.S. Cl.
CPC .......... C07C 309/10 (2013.01); C07C 381/12 (2013.01); G03F 7/0045 (2013.01); C07C 2603/74 (2017.05)

(58) Field of Classification Search
CPC .......................... C07C 381/12; C07C 309/10
See application file for complete search history.

(56) References Cited

U.S. PATENT DOCUMENTS

| | | | |
|---|---|---|---|
| 5,128,232 A | 7/1992 | Thackeray et al. | |
| 9,023,581 B2 * | 5/2015 | Kawaue | C07C 309/10 430/270.1 |
| 10,248,019 B2 * | 4/2019 | Kataoka | C07C 309/13 |
| 2009/0258315 A1 | 10/2009 | Ober et al. | |
| 2012/0129104 A1 | 5/2012 | Aqad et al. | |
| 2012/0219913 A1 * | 8/2012 | Kataoka | G03F 7/0397 430/285.1 |
| 2013/0137038 A1 | 5/2013 | Li et al. | |
| 2015/0044509 A1 * | 2/2015 | Kunimoto | C07C 309/08 428/704 |
| 2016/0004157 A1 | 1/2016 | Ito et al. | |

FOREIGN PATENT DOCUMENTS

| | | |
|---|---|---|
| EP | 0164248 A2 | 12/1985 |
| EP | 1586570 A1 | 10/2005 |
| EP | 2584409 A1 | 4/2013 |
| JP | 2005-148291 A | 6/2005 |
| JP | 2009-294394 A | 12/2009 |
| JP | 2013-147485 A | 8/2013 |
| JP | 2016-204370 | 12/2016 |
| WO | 2007/124092 A2 | 11/2007 |
| WO | 2007/124092 A3 | 11/2007 |
| WO | 2013/099662 A1 | 7/2013 |

OTHER PUBLICATIONS

Yi et al., Sulfonium Salts of Alicyclic Group Functionalized Semifluorinated Alkyl Ether Sulfonates As Photoacid Generators, Chemistry of Materials, 21(17), 4037-4046 (2009). (Year: 2009).*
International Search Report and Written Opinion dated Jun. 18, 2019 by the European Patent Office for counterpart international patent application No. PCT/US2019/022252.
Office Action dated Dec. 14, 2021 by the Japanese Patent Office for counterpart Japanese Patent Application No. 2020-547339 (with English translation).

* cited by examiner

*Primary Examiner* — Amanda C. Walke
(74) *Attorney, Agent, or Firm* — Stradley Ronon Stevens & Young, LLP

(57) ABSTRACT

Novel photoacid generator compounds are provided. Compositions that include the novel photoacid generator compounds are also provided. The present disclosure further provides methods of making and using the photoacid generator compounds and compositions disclosed herein. The compounds and compositions are useful as photoactive components in chemically amplified resist compositions for various microfabrication applications.

20 Claims, No Drawings

CYCLIC SULFONATE COMPOUNDS AS PHOTOACID GENERATORS IN RESIST APPLICATIONS

CROSS-REFERENCE TO RELATED APPLICATION

This application is a U.S. National Phase filing of international patent application number PCT/US2019/022252, filed on Mar. 14, 2019 that claims priority to U.S. provisional patent application Ser. No. 62/644,288, filed on Mar. 16, 2018, the entireties of which are incorporated herein by reference.

TECHNICAL FIELD

The present disclosure relates to new photoacid generator compounds ("PAGs") and compositions that comprise such PAG compounds. In particular, the PAG compounds of the present disclosure have excellent solubility in organic solvents and exhibit higher sensitivity and better performance in a photolithographic process than conventional PAG compounds.

BACKGROUND

Photoresists are photosensitive films for transfer of images to a substrate. They form negative or positive images. After coating a photoresist on a substrate, the coating is exposed through a patterned photomask to a source of activating energy, such as ultraviolet light, to form a latent image in the photoresist coating. The photomask has areas opaque and transparent to activating radiation that define an image desired to be transferred to the underlying substrate.

Chemical amplification-type photoresists have proven to be useful in achieving high sensitivity in processes for forming ultrafine patterns in the manufacture of semiconductors. These photoresists are prepared by blending a PAG with a polymer matrix having acid labile structures. According to the reaction mechanism of such a photoresist, the photoacid generator generates acid when it is irradiated by the light source, and the main chain or branched chain of the polymer matrix in the exposed or irradiated portion reacts in a so called "post exposure bake"(PEB) with the generated acid and is decomposed or cross-linked, so that the polarity of the polymer is altered. This alteration of polarity results in a solubility difference in the developing solution between the irradiated exposed area and the unexposed area, thereby forming a positive or negative image of a mask on the substrate. Acid diffusion is important not only to increase photoresist sensitivity and throughput, but also to limit line edge roughness due to shot noise statistics.

In a chemically amplified photoresist, the solubility-switching chemistry necessary for imaging is not caused directly by the exposure; rather exposure generates a stable catalytic species that promotes solubility-switching chemical reactions during the subsequent PEB step. The term "chemical amplification" arises from the fact that each photochemically-generated catalyst molecule can promote many solubility-switching reaction events. The apparent quantum efficiency of the switching reaction is the quantum efficiency of catalyst generation multiplied by the average catalytic chain length. The original exposure dose is "amplified" by the subsequent chain of chemical reaction events. The catalytic chain length for a catalyst can be very long (up to several hundred reaction events) giving dramatic exposure amplification.

Chemical amplification is advantageous in that it can greatly improve resist sensitivity, but it is not without potential drawbacks. For instance as a catalyst molecule moves around to the several hundred reactions sites, nothing necessarily limits it to the region that was exposed to the imaging radiation. There is a potential trade-off between resist sensitivity and imaging fidelity. For example, the amplified photoresist is exposed through a photomask, generating acid catalyst in the exposed regions. The latent acid image generated in the first step is converted into an image of soluble and insoluble regions by raising the temperature of the wafer in the PEB, which allows chemical reactions to occur. Some acid migrates out of the originally exposed region causing "critical dimension bias" problems. After baking, the image is developed with a solvent. The developed feature width may be larger than the nominal mask dimension as the result of acid diffusion from exposed into the unexposed regions. For much of the history of amplified resists this trade-off was of little concern as the catalyst diffusion distances were insignificant relative to the printed feature size, but as feature sizes have decreased, the diffusion distances have remained roughly the same and catalyst diffusion has emerged as a significant concern.

In order to generate enough acid which would change the solubility of the polymer, a certain exposure time is required. For a known PAG molecule like N-Hydroxynaphthalimide triflate ("NIT"), this exposure time is rather long (due to its low absorption at 365 nm or longer). Increasing the concentration of such PAGs, however, will not result in faster exposure times because the solubility of the PAG is the limiting factor. Another possibility is to add sensitizers which absorb the light and transfer energy to the PAG which would then liberate the acid. Such sensitizers, however, must be used in rather high concentrations in order to be able to transfer the energy to a PAG in close proximity. At such high concentrations, sensitizers often have an absorption which is too high and has negative effects on the shape of the resist profile after development.

Higher sensitivity is also needed in any application where effects based on a photo generation of acid is used. In addition to resist applications these applications could be for photo-induced polymerization, photo-induced crosslinking, photo-induced degradation, photo-induced deprotection, photo-induced color change or photo-induced transformation of functional groups or any combination of at least two of them.

Accordingly, there is a need in the art for PAGs that exhibit better a solubility, which means that more active molecules are imparted into the formulation, wherein a composition comprising these compounds has a high sensitivity towards electromagnetic radiation, in particular towards electromagnetic radiation with a wavelength of 200 to 500 nm, and—at the same time—allows the production of a patterned structure with a higher resolution, compared to the photoresist compositions known from the prior art.

SUMMARY

The present disclosure satisfies this need by providing sulfonic acid derivative compound represented by Formula (I):

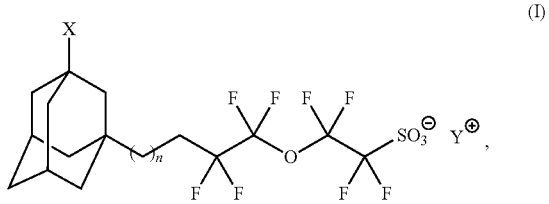

wherein X is either H or —OH; and Y is a cation selected from either Formula A or B:

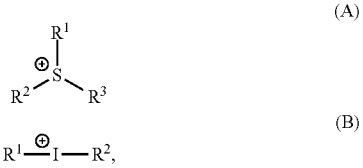

wherein $R^1$, $R^2$, and $R^3$ are each independently selected from the group consisting of a vinyl group, an allyl group, optionally substituted ($C_1$-$C_{20}$)alkyl group, and an optionally substituted ($C_6$-$C_{15}$)aralkyl group, wherein $R^1$ and $R^2$ may be joined together along with the sulfur to which they are attached to form a ring; and n is an integer from 1 to 10.

In some embodiments, the present disclosure also provides resist compositions comprising imaging-effective amounts of one or more PAG according to the present disclosure and a resin.

In other embodiments, the present disclosure provides methods for forming relief images of the photoresists of the present disclosure, including methods for forming highly resolved patterned photoresist images (e.g., a patterned line having essentially vertical sidewalls) of sub-quarter micron dimensions or less, such as sub-0.2 or sub-0.1 micron dimensions.

The present disclosure further provides articles of manufacture comprising substrates such as a microelectronic wafer or a flat panel display substrate having coated thereon the photoresists and relief images of the present disclosure. Other aspects of the present disclosure are disclosed infra.

DETAILED DESCRIPTION

Definitions

Unless otherwise stated, the following terms used in this Application, including the specification and claims, have the definitions given below. It must be noted that, as used in the specification and the appended claims, the singular forms "a," "an," and "the" include plural referents unless the context clearly dictates otherwise.

All numerical designations, such as, weight, pH, temperature, time, concentration, and molecular weight, including ranges, are approximations which are varied by 10%. It is to be understood, although not always explicitly stated, that all numerical designations are preceded by the term "about." It also is to be understood, although not always explicitly stated, that the reagents described herein are merely exemplary and that equivalents of such are known in the art.

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, the term "moiety" refers to a specific segment or functional group of a molecule. Chemical moieties are often recognized chemical entities embedded in or appended to a molecule.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing from 1-20 (e.g., 2-18, 3-18, 1-8, 1-6, 1-4, or 1-3) carbon atoms. An alkyl group can be straight, branched, cyclic or any combination thereof. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents or can be multicyclic as set forth below.

Unless specifically limited otherwise, the term "alkyl," as well as derivative terms such as "alkoxy" and "thioalkyl," as used herein, include within their scope, straight chain, branched chain and cyclic moieties.

As used herein, an "alkenyl" group refers to an aliphatic carbon group that contains from 2-20 (e.g., 2-18, 2-8, 2-6, or 2-4) carbon atoms and at least one double bond. Like an alkyl group, an alkenyl group can be straight, branched or cyclic or any combination thereof. Examples of an alkenyl group include, but are not limited to, allyl, isoprenyl, 2-butenyl, and 2-hexenyl. An alkenyl group can be optionally substituted with one or more substituents as set forth below.

As used herein, an "alkynyl" group refers to an aliphatic carbon group that contains from 2-20 (e.g., 2-8, 2-6, or 2-4) carbon atoms and has at least one triple bond. An alkynyl group can be straight, branched or cyclic or any combination thereof. Examples of an alkynyl group include, but are not limited to, propargyl and butynyl. An alkynyl group can be optionally substituted with one or more substituents as set forth below.

As used herein, the term "alicyclic" refers to an aliphatic ring compound or group comprising at least three carbon atoms and the bonds between pairs of adjacent atoms may all be of the type designated single bonds (involving two electrons), or some of them may be double or triple bonds (with four or six electrons, respectively).

A "halogen" is an atom of the 17th Group of the period table, which includes fluorine, chlorine, bromine and iodine.

As used herein, an "aryl" group used alone or as part of a larger moiety as in "aralkyl," "aralkoxy," or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents as set forth below.

As used herein, an "aralkyl" or "arylalkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, azacycloalkyl, or ((aminocarbonyl)cycloalkyl)cycloalkyl.

As used herein, the term "heteroaryl" group refers to a monocyclic, bicyclic, or tricyclic ring system having 4 to 18 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,30,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents as is set forth below.

A "heteroarylalkyl" group, as used herein, refers to an alkyl group (e.g., a $C_{1-4}$ alkyl group) that is substituted with a heteroaryl group. Both "alkyl" and "heteroaryl" have been defined above. A heteroarylalkyl is optionally substituted with one or more substituents as is set forth below.

As used herein, an "acyl" group refers to a formyl group or $R^X$—C(O)— (such as -alkyl-C(O)—, also referred to as "alkylcarbonyl") where "alkyl" have been defined previously.

As used herein, the term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups.

As used herein, an "alkoxy" group refers to an alkyl-O— group where "alkyl" has been defined previously.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, "Alkoxycarbonyl" means —COOR where R is alkyl as defined above, e.g., methoxycarbonyl, ethoxycarbonyl, and the like.

As used herein, a "sulfonyl" group refers to —S(O)$_2$—R$^x$ when used terminally and —S(O)$_2$— when used internally.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. In certain embodiments, lower alkylthios are contemplated.

As used herein, the term "amine" or "amino" includes compounds where a nitrogen atom is covalently bonded to at least one carbon or heteroatom. The term "amine" or "amino" also includes —NH$_2$ and also includes substituted moieties. The term includes "alkyl amino" which comprises groups and compounds wherein the nitrogen is bound to at least one additional alkyl group. The term includes "dialkyl amino" groups wherein the nitrogen atom is bound to at least two additional independently selected alkyl groups. The term includes "arylamino" and "diarylamino" groups wherein the nitrogen is bound to at least one or two independently selected aryl groups, respectively.

The term "haloalkyl" refers to alkyl groups substituted with from one up to the maximum possible number of halogen atoms. The terms "haloalkoxy" and "halothioalkyl" refer to alkoxy and thioalkyl groups substituted with from one up to five halogen atoms.

The phrase "optionally substituted" is used interchangeably with the phrase "substituted or unsubstituted." As described herein, compounds of the present disclosure can optionally be substituted with one or more substituents, such as are illustrated generally above, or as exemplified by particular classes, subclasses, and species of the present disclosure. As described herein any of the above moieties or those introduced below can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this present disclosure are those combinations that result in the formation of stable or chemically feasible compounds.

Although the drawings show only one isomer with respect to the constitution at the double bond this does not mean that only this isomer is meant but rather displays one isomer as representative for all isomers. Hence the cis- as well as the trans-isomers as well as mixtures of the two are included in the general description of the compounds and structures.

Modifications or derivatives of the compounds disclosed throughout this specification are contemplated as being useful with the methods and compositions of the present disclosure. Derivatives may be prepared and the properties of such derivatives may be assayed for their desired properties by any method known to those of skill in the art. In certain aspects, "derivative" refers to a chemically modified compound that still retains the desired effects of the compound prior to the chemical modification.

Sulfonic Acid Derivate Photoacid Generator Compounds

The sulfonic acid derivative compounds according to the present disclosure can be used as photoacid generators as will be explained in more detail below. Surprisingly, it has been discovered that PAG compounds of the present disclosure are characterized by excellent solubility and photoreactivity towards electromagnetic radiation, in particular towards electromagnetic radiation with a wavelength in the range from 150 to 500 nm, preferably in the range from 300 to 450 nm, more preferably in the range from 350 to 440 nm, more preferably at wavelengths of 365 nm (i-line), 405 nm (h-line) and 436 nm (g-line).

The sulfonic acid derivative compounds according to the present disclosure are N-hydroxynaphthalimide sulfonate derivatives represented by Formula (I):

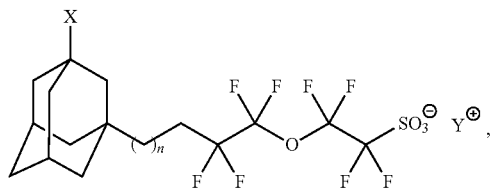
(I)

wherein X is either H or —OH; and Y is a cation selected from either Formula A or B:

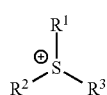
(A)

(B)

wherein $R^1$, $R^2$, and $R^3$ are each independently selected from the group consisting of a vinyl group, an allyl group, optionally substituted ($C_1$-$C_{20}$)alkyl group, and an optionally substituted ($C_6$-$C_{15}$)aralkyl group, wherein $R^1$ and $R^2$ may be joined together along with the sulfur to which they are attached to form a ring; and n is an integer from 1 to 10.

In some embodiments, $R^1$, $R^2$, and $R^3$ in Formula (I)(A) is an optionally substituted ($C_6$-$C_{15}$)aralkyl group. Examples of such PAG compounds include those in Table 1:

TABLE 1

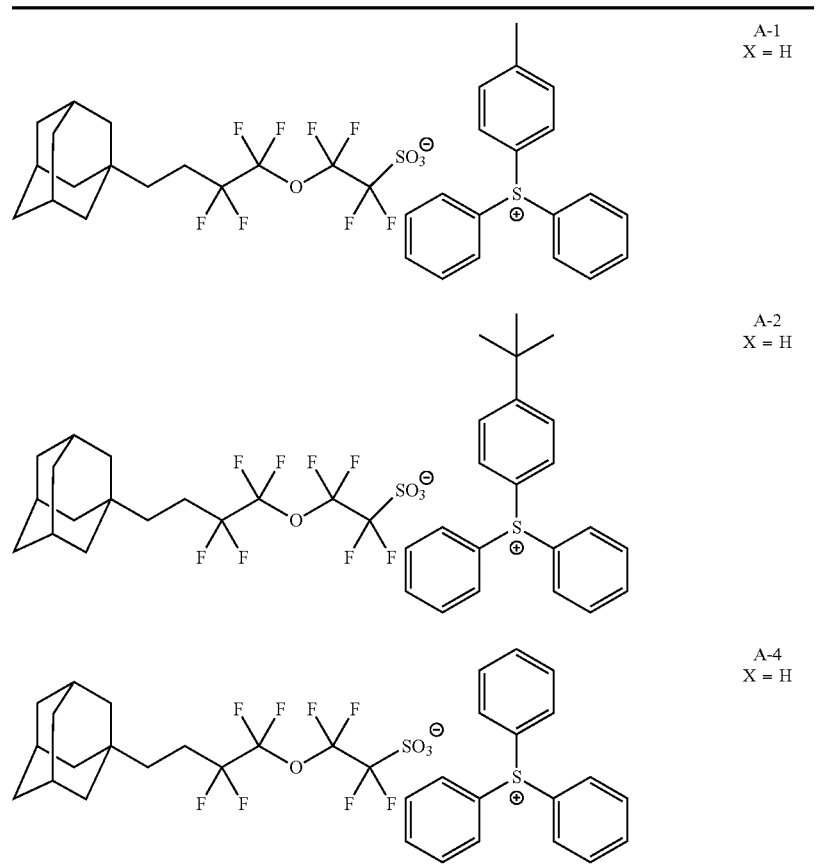

A-1
X = H

A-2
X = H

A-4
X = H

TABLE 1-continued
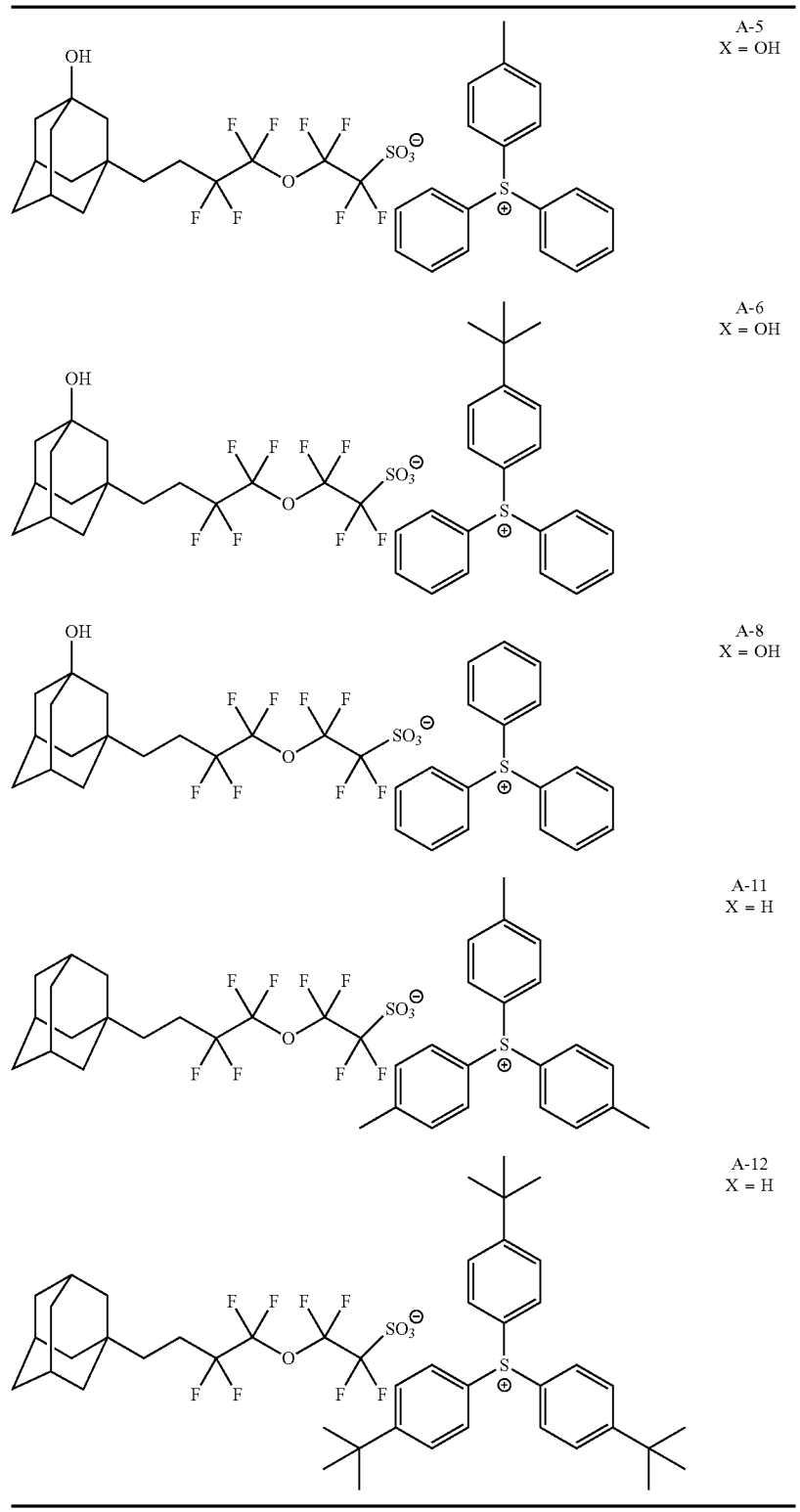
In other embodiments $R^1$ and $R^2$ in Formula (I)(A) are joined together along with the sulfur to which they are attached to form a ring and $R^3$ is an optionally substituted $(C_6-C_{15})$aralkyl group. Examples of such PAG compounds include those in Table 2:

TABLE 2

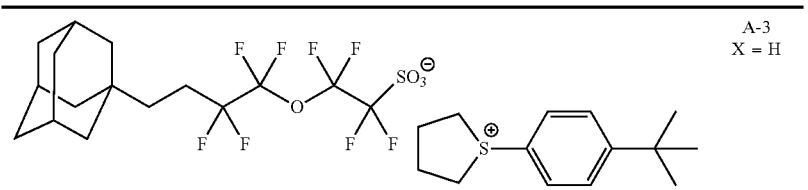

A-3
X = H

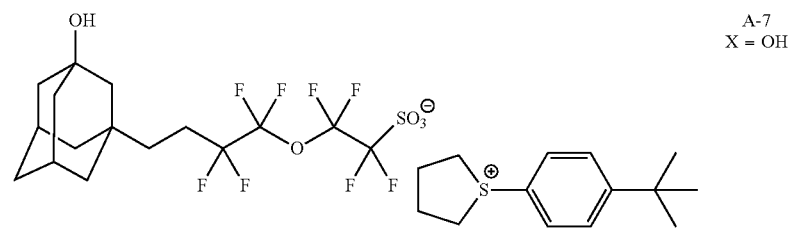

A-7
X = OH

In other embodiments $R^1$ and $R^2$ in Formula (I)(B) are each an optionally substituted ($C_6$-$C_{15}$)aralkyl group. Examples of such PAG compounds include those in Table 3:

TABLE 3

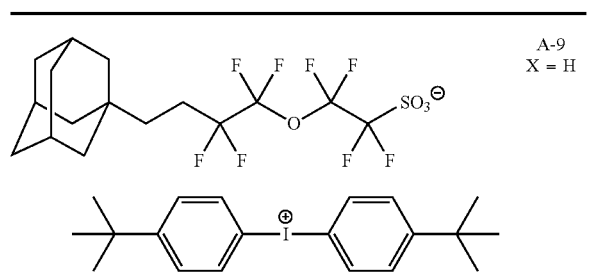

A-9
X = H

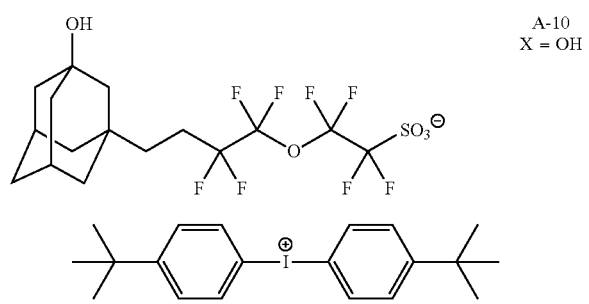

A-10
X = OH

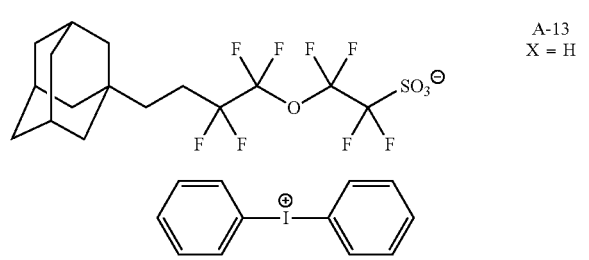

A-13
X = H

TABLE 3-continued

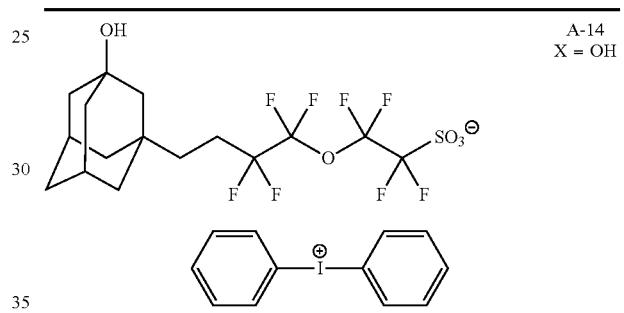

A-14
X = OH

PAGs according to the present disclosure impart a high degree of efficiency to the photolithography process and leads to enhanced contrast and resolution between exposed and unexposed regions of the resist composition. The amount of PAG and the energy supplied by the UV irradiation are chosen such that they are sufficient to allow the desired polycondensation.

Compounds of the present disclosure generate acids upon irradiating with, for example, an ArF excimer laser. Compounds of the present disclosure also exhibit high solubility in organic solvents such as PGMEA. Table 4 shows the solubility of a sample of the compounds disclosed herein in a PGMEA solvent.

TABLE 4

| Property | A-1 | A-2 | A-3 | A-4 |
| --- | --- | --- | --- | --- |
| Solubility (wt %) PGMEA | >50% | 29% | 71% | >50% |

PAGs of the present disclosure may be suitably used in positive-acting or negative-acting chemically amplified photoresists, i.e., negative-acting resist compositions which undergo a photoacid-promoted cross-linking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions.

Preferred imaging wavelengths for photoresists of the present disclosure include sub-300 nm wavelengths, e.g., 248 nm, and sub-200 nm wavelengths, e.g., 193 nm and EUV, more preferably in the range from 200 to 500 nm, preferably in the range from 300 to 450 nm, even more preferably in the range from 350 to 440 nm, most preferably at wavelengths of 365 nm (i-line), 405 (h-line) and 436 nm (g-line).

Synthesis of Compounds

There is no particular limitation for the method for synthesizing the adamantane-containing sulfonate compounds disclosed herein, and any well-known approach can be used for the synthesis of these compounds. The synthesis of compound A1 was shown in Scheme 1.

Scheme 1. Synthesis of compound A1.

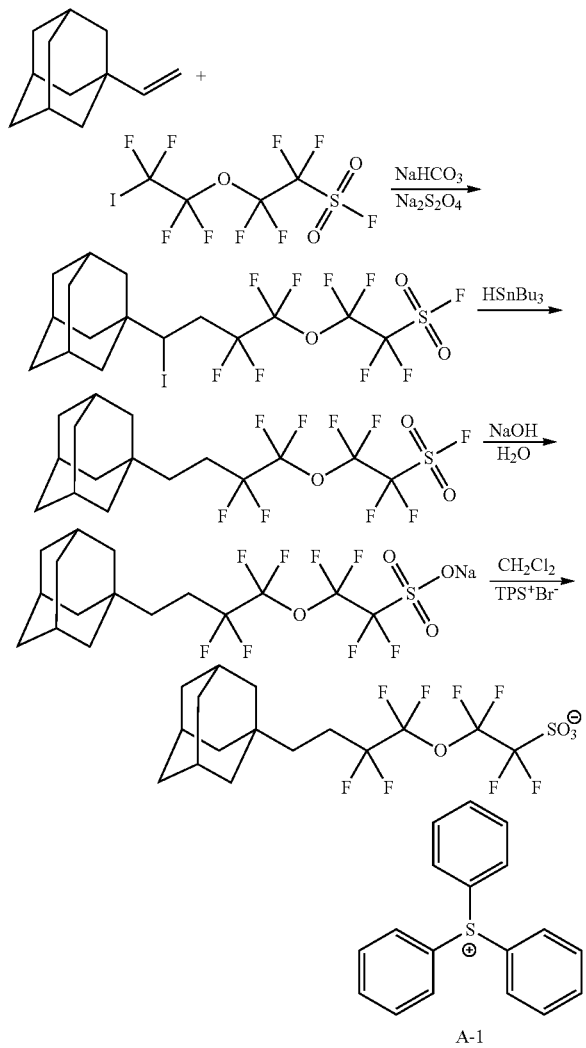

A-1

Compositions

Compositions of the present disclosure comprise (i) at least one photoacid generator of Formula (I); (ii) at least one compound which is capable of being imparted with an altered solubility in an aqueous solution in the presence of an acid; (iii) an organic solvent; and, optionally, (iv) an additive.

Compositions according to the present disclosure comprising the photoacid generators of Formula (I) are suitable for use as a photoresist in a variety of applications, in particular for the production of electronic devices, including flat panel display (in this case the photoresist can be coated glass substrate or a layer of indium tin oxide) and a semiconductor device (in this case the photoresist can be coated onto a silicon wafer substrate). Compositions comprising the photoacid generators of Formula (I) are suitable for photo-induced polymerization, photo-induced crosslinking, photo-induced degradation, photo-induced deprotection, photo-induced color change or photo-induced transformation of functional groups or any combination of at least two of them. Various exposure radiations can be used, including an exposure with electromagnetic radiation having a wavelength of 200 to 500 nm, preferably in the range from 300 to 450 nm, more preferably in the range from 350 to 440 nm, even more preferably at 365 nm (i-line), 436 nm (g-line) or 405 nm (h-line), wherein an electromagnetic radiation with a wavelength of 365 nm is particularly preferred.

The photoresist compositions according to the present disclosure comprise as component (ii) one or more photoresist polymers or copolymers, which may be soluble or insoluble in a developer solution. The photoresist compositions according to the present disclosure may be for positive tone or negative tone composition. In the case of a positive tone composition the solubility of component (ii) is increased upon reaction with the acid released from the compound according to the present disclosure. In this case, photoresist polymers or copolymers with acid labile groups are used as component (ii) which are insoluble in aqueous base solution, but which in the presence of the acid are catalytically de-protected such that they become soluble in solution. In the case of a negative tone composition, the solubility of component (ii) is decreased upon reaction with the acid released from the compound according to the present disclosure. In this case, photoresist polymers or copolymers are used as component (ii) which are soluble in the developer solution, but are cross-linked in the presence of the acid such that they become insoluble in an aqueous base solution. Thus, photoresist polymers or copolymers are capable of being imparted with an altered solubility in a developer solution in the presence of an acid. Preferably the developer solution is an aqueous solution, more preferably it is an aqueous base solution.

Examples of photoresist polymers that may be used as component (ii) in a positive tone composition include without limitation, aromatic polymers, such as homopolymers or copolymers of hydroxystyrene protected with an acid labile group; acrylates, such as for example, poly(meth)acrylates with at least one unit containing a pendant alicyclic group, and with the acid labile group being pendant from the polymer backbone and/or from the aclicyclic group, cycloolefin polymers, cycloolefin maleic anhydride copolymers, cycloolefin vinyl ether copolymers, siloxanes; silsesquioxanes, carbosilanes; and oligomers, including polyhedral oligomeric silsesquioxanes, carbohydrates, and other cage compounds. The foregoing polymers or oligomers are appropriately functionalized with aqueous base soluble groups, acid-labile groups, polar functionalities, and silicon containing groups as needed.

Examples of copolymers that may be used as component (ii) in the positive tone compositions of the present disclosure include without limitation poly(p-hydroxystyrene)-methyl adamantyl methacrylate (PHS-MAdMA), poly(p-hydroxystyrene)-2-ethyl-2-adamantyl methacrylate (PHS-EAdMA), poly(p-hydroxystyrene)-2-ethyl-2-cyclopentyl methacrylate (PHS-ECpMA), poly(p-hydroxy-styrene)-2-methyl-2-cyclopentyl methacrylate (PHS-MCpMA) or PHS-EVE.

Preferably, the at least one component (ii) in a positive tone composition is a poly(hydroxystyrene)-resin in which at least a part of the hydroxy groups is substituted by protective groups. Preferred protective groups are selected from the group consisting of a tert-butoxycarbonyloxy group, a tert-butyloxy group, a tert-amyloxycarbonyloxy group and an acetal group. Furthermore suitable as component ii) are all the polymers and copolymers which in paragraphs [0068] to [0114] of EP 1 586 570 A1 are described as "acid-dissociable group-containing resin." The disclosure of EP 1 586 570 A1 with respect to these resins is incorporated herein by reference a forms a part of the present disclosure.

Preferred negative tone compositions comprise a mixture of materials that will cure, crosslink or harden upon exposure to acid. Preferred negative acting compositions comprise, as component (ii), a polymer binder such as a phenolic or non-aromatic polymer, a cross-linker component as an additive (iv) and the photoacid generator component according to the present disclosure as component (i). Suitable polymer binders and cross-linkers for such negative active photoresist compositions and the use thereof have been disclosed in EP-A-0 164 248 and U.S. Pat. No. 5,128,232. Preferred phenolic polymers for use as component (ii) include novolaks and poly(vinylphenol)s. Novolak resins are the thermoplastic condensation products of a phenol and an aldehyde. Examples of suitable phenols for condensation with an aldehyde, especially formaldehyde, for the formation of novolak resins include phenol, m-cresol, o-cresol, p-cresol, 2,4-xylenol, 2,5-xylenol, 3,4-xylenol, 3,5-xylenol and thymol. An acid catalyzed condensation reaction results in the formation of a suitable novolak resin which may vary in molecular weight from about 500 to 100,000 Daltons. Polyvinyl phenol resins are thermoplastic polymers that may be formed by block polymerization, emulsion polymerization or solution polymerization of the corresponding monomers in the presence of a cationic catalyst. Vinylphenols useful for the production of polyvinyl phenol resins may be prepared, for example, by hydrolysis of commercially available coumarin or substituted coumarins, followed by decarboxylation of the resulting hydroxy cinnamic acids. Useful vinylphenols may also be prepared by dehydration of the corresponding hydroxy alkyl phenols or by decarboxylation of hydroxy cinnamic acids resulting from the reaction of substituted or non-substituted hydroxybenzaldehydes with malonic acid. Preferred polyvinyl phenol resins prepared from such vinylphenols have a molecular weight range of from about 2,000 to about 60,000 daltons. Preferred cross-linkers for use as component (iv) include amine-based materials, including melamine, glycolurils, benzoguanamine-based materials and urea-based materials. Melamine-formaldehyde polymers are often particularly suitable. Such cross-linkers are commercially available, e.g., the melamine polymers, glycoluril polymers, urea-based polymer and benzoguanamine polymers, such as those sold by Cytec under trade names Cymel™ 301, 303, 1170, 1171, 1172, 1123 and 1125 and Beetle™ 60, 65 and 80.

As component (iii) the composition according to the present disclosure comprises at least one organic solvent. The organic solvent may be any solvent capable of dissolving the component (ii) and the component (i) to generate a uniform solution, and one or more solvents selected from known materials used as the solvents for conventional chemically amplified resists can be used. Specific examples of the organic solvent include ketones such as acetone, methyl ethyl ketone, cyclohexanone, methyl isoamyl ketone and 2-heptanone, water, polyhydric alcohols and derivatives thereof such as ethylene glycol, ethylene glycol monoacetate, diethylene glycol, diethylene glycol monoacetate, propylene glycol, propylene glycol monoacetate, dipropylene glycol, or the monomethyl ether, monoethyl ether, monopropyl ether, monobutyl ether or monophenyl ether of dipropylene glycol monoacetate, cyclic ethers such as dioxane, and esters such as methyl lactate, ethyl lactate (EL), methyl acetate, ethyl acetate, butyl acetate, methyl pyruvate, ethyl pyruvate, methyl methoxypropionate, and ethyl ethoxypropionate. These organic solvents can be used alone, or as a mixed solvent containing two or more different solvents. Particularly preferred organic solvents (iii) are selected from the group consisting of a ketone, an ether and ester.

Furthermore, the composition according to the present disclosure may also, optionally, comprise at least one additive being different from components (i), (ii) and (iii). For example, other optional additives include actinic and contrast dyes, anti-striation agents, plasticizers, speed enhancers, sensitizers, crosslinkers, monomers, polymers, binders, stabilizers, absorbers, fillers etc. Such optional additives typically will be in minor concentration in a photoresist composition except for fillers, binders, polymers, monomers and dyes which may be in relatively large concentrations such as, e.g., in amounts of from 5 to 80 percent by weight of the total weight of a resist's dry components.

One additive typically employed in photoresist compositions according to the present disclosure is a basic quencher. The basic quencher is for purposes of neutralizing acid generated in the surface region of the underlying photoresist layer by stray light which reaches what are intended to be unexposed (dark) regions of the photoresist layer. This allows for improvement in depth of focus in the defocus area and exposure latitude by controlling unwanted deprotection reaction in the unexposed areas. As a result, irregularities in the profile, for example, necking and T-topping, in formed resist patterns can be minimized or avoided.

To allow for effective interaction between the basic quencher and the acid generated in the dark areas of the underlying photoresist layer, the basic quencher should be of a non-surfactant-type. That is, the basic quencher should not be of a type that migrates to the top surface of the overcoat layer due, for example, to a low surface free energy relative to other components of the overcoat composition. In such a case, the basic quencher would not be appreciably at the photoresist layer interface for interaction with the generated acid to prevent acid deprotection. The basic quencher should therefore be of a type that is present at the overcoat layer/photoresist layer interface, whether being uniformly dispersed through the overcoat layer or forming a graded or segregated layer at the interface. Such a segregated layer can be achieved by selection of a basic quencher having a high surface free energy relative to other components of the overcoat composition.

Suitable basic quenchers include, for example: linear and cyclic amides and derivatives thereof such as N,N-bis(2-hydroxyethyl)pivalamide, N,N-Diethylacetamide, N1,N1,N3,N3-tetrabutylmalonamide, 1-methylazepan-2-one, 1-allylazepan-2-one and tert-butyl 1,3-dihydroxy-2-(hydroxymethyl)propan-2-ylcarbamate; aromatic amines such as pyridine, and di-tert-butyl pyridine; aliphatic amines such as triisopropanolamine, n-tert-butyldiethanolamine, tris(2-acetoxy-ethyl)amine, 2,2',2",2'''-(ethane-1,2-diylbis(azanetriyl))tetraethanol, and 2-(dibutylamino)ethanol, 2,2', 2"-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate and N (2-acetoxy-ethyl)morpholine. Of these basic quenchers, 1-(tert-butoxycarbonyl)-4-hydroxypiperidine and triisopropanolamine are preferred. While the content of the basic quencher will depend, for example, on the content of the photoacid generator in the underlying photoresist layer, it is typically present in an amount of from 0.1 to 5 wt %, preferably from 0.5 to 3 wt %, more preferably from 1 to 3 wt %, based on total solids of the overcoat composition.

Another concept is to attach a basic moiety to the PAG molecule. In this case the quencher is a part of the PAG and in close proximity to the acid formed upon irradiation. These compounds have a high sensitivity towards electromagnetic radiation, in particular towards electromagnetic radiation with a wavelength in the range of 200 to 500 nm, more particularly towards electromagnetic radiation with a wavelength of 365 nm (i-line), and—at the same time—allows the production of a patterned structure with a higher resolution, compared to the photoresist compositions known from the prior art containing quenchers as additives.

The resin binder component of resists of the present disclosure are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

According to a preferred embodiment, the compositions according to the present disclosure comprise:
(i) 0.05 to 15 wt. %, preferably 0.1 to 12.5 wt. % and most preferably 1 to 10 wt. % of at least one photoacid generator compound of Formula (I);
(ii) 5 to 50 wt. %, preferably 7.5 to 45 wt. % and most preferably 10 to 40 wt. % of at least one photoresist polymer or copolymer which may be base soluble or insoluble; and
(iv) 0 to 10 wt. %, preferably 0.01 to 7.5 wt. % and most preferably 0.1 to 5 wt. % of the further additive, wherein the reminder in the composition is the organic solvent (iii).

As in the compounds according to the present disclosure the functional basic group serving as a quencher for the acid group that is released upon exposure to electromagnetic radiation is a part of the photoacid generator compound, it is not necessary to add a separate basic component as a quencher (as it is necessary in the photoresist compositions known from the prior art). According to a preferred embodiment of the composition according to the present disclosure this composition preferably comprises less than 5 wt. %, more preferably less than 1 wt. %, even more preferably less than 0.1 wt. %, and most preferably 0 wt. % of a basic compound being different from components (i) through (iv), such as hydroxides, carboxylates, amines, imines, and amides.

The photoresists of the present disclosure are generally prepared following known procedures with the exception that a PAG of the present disclosure is substituted for prior photoactive compounds used in the formulation of such photoresists. For example, a resist of the present disclosure can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether; lactates such as ethyl lactate or methyl lactate, with ethyl lactate being preferred; propionates, particularly methyl propionate and ethyl propionate; a Cellosolve ester such as methyl Cellosolve acetate; an aromatic hydrocarbon such toluene or xylene; or a ketone such as methylethyl ketone, cyclohexanone and 2-heptanone. Typically the solids content of the photoresist varies between 5 and 35 percent by weight of the total weight of the photoresist composition.

The photoresist compositions of the present disclosure can be used in accordance with known procedures. Though the photoresists of the present disclosure may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and non-exposed regions of the resist coating layer, and then developed preferably with an aqueous alkaline developer to form a relief image. The substrate on which a resist of the present disclosure is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, e.g., glass substrates, indium tin oxide coated substrates and the like. A liquid coating resist composition may be applied by any standard means such as spinning, dipping or roller coating. The exposure energy should be sufficient to effectively activate the photoactive component of the radiation sensitive system to produce a patterned image in the resist coating layer. Suitable exposure energies typically range from about 1 to 300 mJ/cm$^2$. As discussed above, preferred exposure wavelengths include sub-200 nm such as 193 nm. Suitable post-exposure bake temperatures are from about 50° C. or greater, more specifically from about 50 to 140° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

Composites

The present disclosure provides a process for producing a composite comprising a substrate and a coating that is applied onto the substrate in a patterned structure, the process comprising the steps of:
(a) applying a layer of the composition according to the present disclosure onto the surface of the substrate and at least partial removal of the organic solvent (iii);

(b) exposing selected areas of the layer to electromagnetic radiation, thereby releasing an acid from the compound
   (i) in the areas exposed to the electromagnetic radiation;
(c) optionally heating the layer to impart compound (ii) in the areas in which the acid has been released with an altered solubility in an aqueous solution; and
(d) optionally, at least partial removal of the layer.

In process step (a), a layer of the composition according to the present disclosure is applied onto the surface of the substrate followed by at least partial removal of the organic solvent (iii).

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Application of the composition according to the present disclosure onto the substrate may be accomplished by any suitable method, including spin coating, curtain coating, spray coating, dip coating, doc-tor blading, or the like. Applying the layer of photoresist is preferably accomplished by spin-coating the photoresist using a coating track, in which the photoresist is dispensed on a spinning wafer. During the spin coating process, the wafer may be spun at a speed of up to 4,000 rpm, preferably from about 500 to 3,000 rpm, and more preferably 1,000 to 2,500 rpm. The coated wafer is spun to remove the organic solvent (iii), and baked on a hot plate to remove residual solvent and free volume from the film to make it uniformly dense.

In process step (b), selected areas of the layer are exposed to electromagnetic radiation, there-by releasing an acid from the compound (i) in the areas exposed to the electromagnetic radiation. As stated above, various exposure radiations can be used, including an exposure with electromagnetic radiation having a wavelength of 365 nm (i-line), 436 nm (g-line) or 405 nm (h-line), wherein electromagnetic radiation having a wavelength of 365 nm is particularly preferred.

Such a pattern-wise exposure can be carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the component according to the present disclosure that is contained in the photoresist layer in the exposed areas and generates acid and decomposition by-products, and that the acid then effects a chemical change in the polymer compound (ii) (de-blocking the acid sensitive group to generate a base-soluble group, or alternatively, catalyzing a cross-linking reaction in the exposed areas). The resolution of such exposure tools may be less than 30 nm. Alternatively the irradiation may be performed using a beam of electromagnetic radiation which is moved across the surface of the formulation whereby the irradiated areas are selected by the movement of the beam.

In process step (c), the layer can optionally be is heated to impart compound (ii) in the areas in which the acid has been released with an altered solubility in an aqueous solution. In this so called "post-exposure bake" the solubility differences between exposed and unexposed regions of the coating layer are created or enhanced. Typically post-exposure bake conditions include temperatures of about 50° C. or greater, more specifically a temperature in the range of from about 50° C. to about 160° C. for 10 seconds to 30 minutes, preferably for 30 to 200 seconds. According to a particular embodiment of the process according to the present disclosure no heat treatment is performed after process step (b) and before (d).

In process step (d) the layer is optionally at least partially removed with an aqueous solution, preferably an aqueous base solution. This can be accomplished by treating the exposed photoresist layer with a suitable developer capable of selectively removing the exposed portions of the film (where the photoresist is positive tone) or removing the unexposed portions of the film (where the photoresist is negative tone). Preferably, the photoresist is positive tone based on a polymer having acid sensitive (de-protectable) groups, and the developer is preferably a metal-ion free tetraalkylammonium hydroxide solution.

The composite made according to the present disclosure is characterized in that it comprises a substrate and a coating applied on the surface of the substrate in a patterned structure, wherein the coating comprises a compound according to the present disclosure.

The use of the photoacid generator compounds of Formula (I) for photo-induced polymerization, photo-induced cross-linking, photo-induced degradation and photo-induced transformation of functional groups is also within the scope of the present disclosure. The compound according to the present disclosure is particularly suitable for use in protective coatings, smart cards, 3D rapid prototyping or additive manufacturing, sacrificial coatings, adhesives, antireflective coatings, holograms, galvano- and plating masks, ion implantation masks, etch resists, chemical amplified resists, light sensing applications, PCB (printed circuit board) patterning, MEMS fabrication, TFT layer pattering on flat panel display, TFT layer pattering on flexible display, pixel pattering for display, in color filters or black matrix for LCD, or semiconductor patterning in packaging process and TSV related patterning on semiconductor manufacturing protective coatings, smart cards, 3D rapid prototyping or additive manufacturing, sacrificial coatings, adhesives, antireflective coatings, holograms, galvano- and plating masks, ion implantation masks, etch resists, chemical amplified resists, light sensing applications or in color filters.

The following Examples are intended to illustrate the above disclosure and should not be construed as to narrow its scope. One skilled in the art will readily recognize that the Examples suggest many other ways in which the present disclosure could be practiced. It should be understood that many variations and modifications may be made while remaining within the scope of the present disclosure.

EXAMPLES

Examples 1, 2, 3, and 4 describe examples of synthesis of the sulfonate compounds according to this invention.

Example 1: Synthesis of Compound I-1

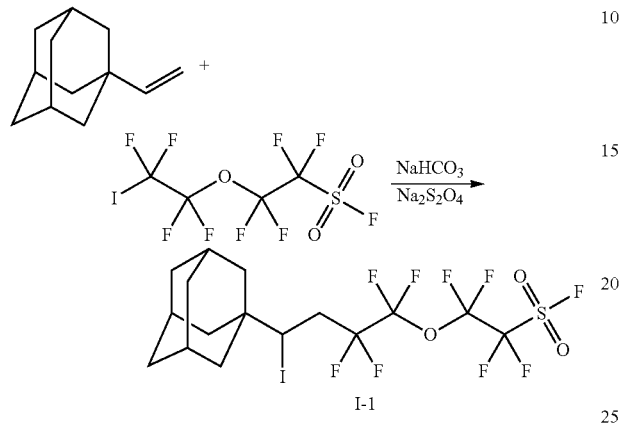

To a 100 mL flask was charged vinyl admantane (5 g, 30.8 mmol), ICF$_2$CF$_2$OCF$_2$CF$_2$SO$_2$F (16.41 g, 38.5 mmol), 12 mL of water and 24 mL of ACN. The mixture was stirred under nitrogen for 10 min. To the mixture was added a mixture of NaHCO$_3$ (1.59 g, 18.5 mmol) and a mixture of sodium bisulfite and sodium metabisulfite (2.15 g). The reaction temperature increased to 36° C. in 10 min. The temperature dropped to 26° C. in 20 min. The mixture was then heated to 40° C. and kept at the same temperature for 2 h. The mixture was cooled down to rt. Filtration and washing with DI water afforded 16.0 g (yield: 88.3%) of compound I-1 under air drying. $^1$H NMR (300 MHz, CDCl$_3$) δ: 3.91 (dd, 1H), 2.95 (m, 1H), 2.65 (m, 1H), 1.95 (br s, 3H), 1.40-1.70 (m, 12H). $^{13}$C NMR (75 MHz, CDCl$_3$) δ: 40.2, 37.1, 36.9, 36.5, 36.2, 28.5.

Example 2: Synthesis of Compound I-2

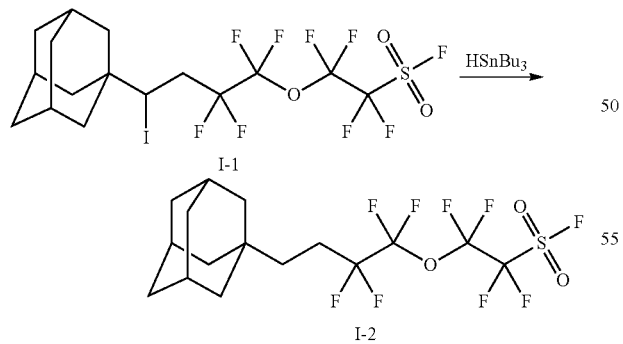

To a 250 mL flask was charged compound I-1 (17.8 g, 30.3 mmol) in 36 g of MTBE. The mixture was heated to 40° C., and tributyltin hydride (9.69 g, 33.3 mmol) was added dropwise to the flask. After the addition, the reaction mixture was stirred at 40° C. overnight. The mixture was cooled down to rt, and 20% of KF was added to the mixture. The mixture was stirred at rt for several hours. The white precipitates were filtered, and the aqueous layer was separated. Removal of solvents under rotavap gave an oily residue which was purified by column chromatography. The final compound I-2 was obtained in 7.1 g (yield: 51%) as a colorless oil. $^1$H NMR (300 MHz, CDCl$_3$) δ: 1.8-2.0 (br m, 5H), 1.61 (pq, 6H), 1.39 (d, 6H), 1.2-1.3 (br m, 2H).

Example 3: Synthesis of Compound I-3

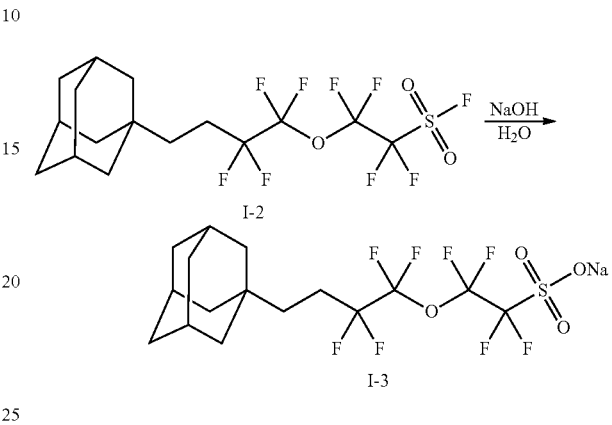

To a 100 mL flask was charged compound I-2 (10 g, 21.6 mmol) and NaOH (1.73 g, 43.3 mmol) in 50 mL of water. The mixture was heated at reflux overnight. The mixture was cooled down to rt. The water was removed under rotavap to give 10.2 g (yield: 100%) of compound I-3 as a waxy solid. The compound I-3 was used in the subsequent reaction without further purification. $^1$H NMR (300 MHz, DMSO) δ: 1.97-2.18 (br m, 2H), 1.93 (br s, 3H), 1.63 (pq, 6H), 1.45 (d, 6H), 1.2-1.3 (br m, 2H).

Example 4: Synthesis of Compound A1

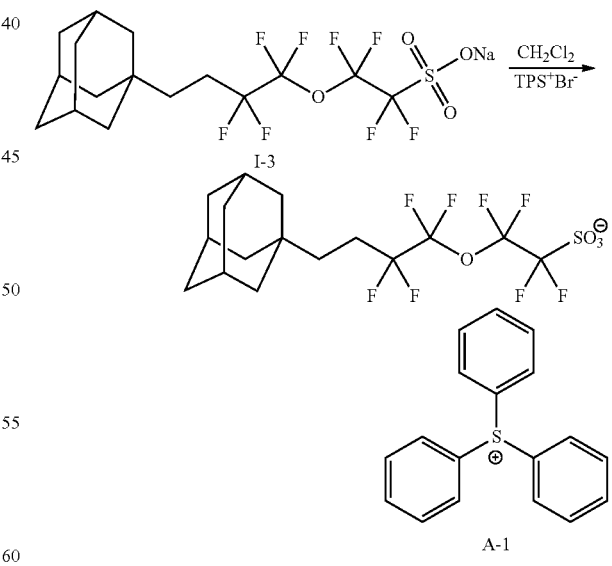

To a 50 mL flask was charged compound I-3 (2.0 g, 4.13 mmol) and triphenylsulfonium bromide (1.42 g, 4.13 mmol) in 10 mL of water. The mixture was cooled down to rt. 10 mL of CH$_2$Cl$_2$ was added. The organic layer was separated. Removal of solvents under rotavap gave 3.0 g of an oily residue. The oily residue was further purified by column chromatography to give 2.4 g (yield: 80%) of compound A1. $^1$H NMR (300 MHz, CDCl$_3$) δ: 7.6-7.8 (br m, 15H), 1.93-2.13 (br m, 2H), 1.87 (br s, 3H), 1.59 (pq, 6H), 1.42 (d, 6H), 1.2-1.3 (br m, 2H). $^{13}$C NMR (75 MHz, CDCl$_3$) δ: 134.7, 131.7, 131.1, 124.3, 41.8, 36.9, 33.8, 31.4, 28.5, 24.1 (t).

Compounds A2, A3, and A4 were similarly synthesized as examples 2, 3, and 4, respectively. Compound A2. $^1$H NMR (300 MHz, CDCl$_3$) δ: 7.6-7.8 (br m, 14H), 1.93-2.13 (br m, 2H), 1.87 (br s, 3H), 1.62 (pq, 6H), 1.42 (d, 6H), 1.34 (s, 9H), 1.2-1.3 (br m, 2H). $^{13}$C NMR (75 MHz, CDCl$_3$) δ: 159.1, 134.5, 131.6, 131.4, 131.1, 128.8, 124.7, 120.5, 41.9, 36.9, 35.5, 33.8, 31.4, 30.8, 28.5, 24.1 (t).

Compound A3. $^1$H NMR (300 MHz, CDCl$_3$) δ: 7.58-7.78 (br m, 4H), 4.15 (m, 2H), 3.64 (m, 2H), 3.55 (m, 4H), 1.93-2.13 (br m, 2H), 1.94 (br s, 3H), 1.64 (pq, 6H), 1.42 (d, 6H), 1.31 (ps, 11H). $^{13}$C NMR (75 MHz, CDCl$_3$) δ: 158.3, 129.6, 128.5, 122.4, 48.6, 41.9, 36.9, 35.3, 33.8, 31.4, 30.8, 29.1, 28.5, 24.1 (t).

Compound A4. $^1$H NMR (300 MHz, CDCl$_3$) δ: 7.4-7.8 (br m, 14H), 2.42 (s, 3H), 1.93-2.13 (br m, 2H), 1.85 (br s, 3H), 1.62 (pq, 6H), 1.42 (d, 6H), 1.2-1.3 (br m, 2H). $^{13}$C NMR (75 MHz, CDCl$_3$) δ: 146.4, 134.5, 132.4, 131.6, 131.2, 130.9, 124.7, 120.5, 41.8, 36.9, 33.8, 31.4, 28.5, 24.1 (t), 21.6.

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the present disclosure. It is expressly intended, for example, that all ranges broadly recited in this document include within their scope all narrower ranges which fall within the broader ranges. In addition, features of one embodiment may be incorporated into another embodiment.

What is claimed is:

1. A sulfonic acid derivative compound represented by Formula (I):

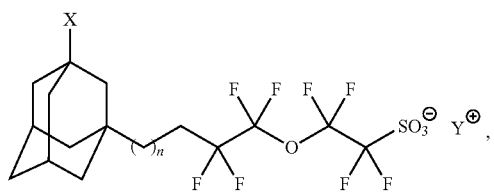

(I)

wherein
X is either H or —OH; and
Y is a cation selected from either Formula A or B:

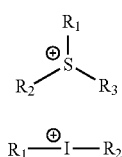

(A)

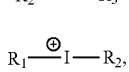

(B)

wherein
$R_1$, $R_2$, and $R_3$ are each independently selected from the group consisting of a vinyl group, an allyl group, optionally substituted ($C_1$-$C_{20}$)alkyl group, and an optionally substituted ($C_6$-$C_{15}$)aralkyl group, wherein $R_1$ and $R_2$ may be joined together along with the sulfur to which they are attached to form a ring; and
n is an integer from 1 to 10.

2. The sulfonic acid derivative compound of claim 1 wherein $R^1$, $R^2$, and $R^3$ are each independently an optionally substituted ($C_6$-$C_{15}$)aralkyl group; and X is H.

3. The sulfonic acid derivative compound of claim 1 wherein $R^1$, $R^2$, and $R^3$ are each independently an optionally substituted ($C_6$-$C_{15}$)aralkyl group; and X is —OH.

4. The sulfonic acid derivative compound of claim 1 wherein $R^1$ and $R^2$ are joined together along with the sulfur to which they are attached to form a ring; $R^3$ is an optionally substituted ($C_6$-$C_{15}$)aralkyl group; and X is H.

5. The sulfonic acid derivative compound of claim 1 wherein $R^1$ and $R^2$ are joined together along with the sulfur to which they are attached to form a ring; $R^3$ is an optionally substituted ($C_6$-$C_{15}$)aralkyl group; and X is —OH.

6. The sulfonic acid derivative compound of claim 1 selected from the group consisting of

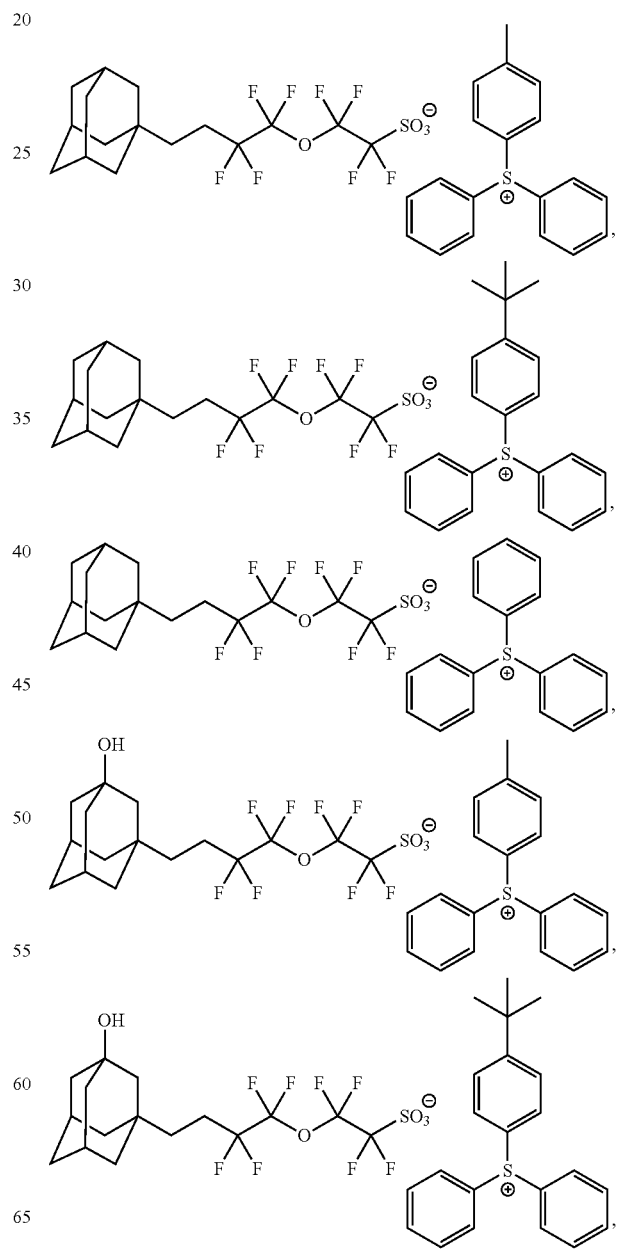

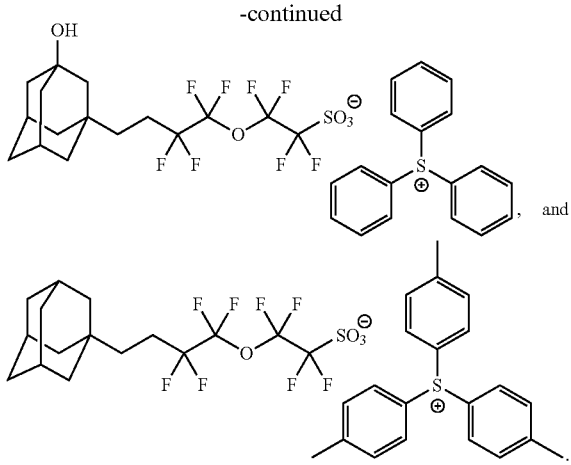

7. The sulfonic acid derivative compound of claim 1 selected from the group consisting of

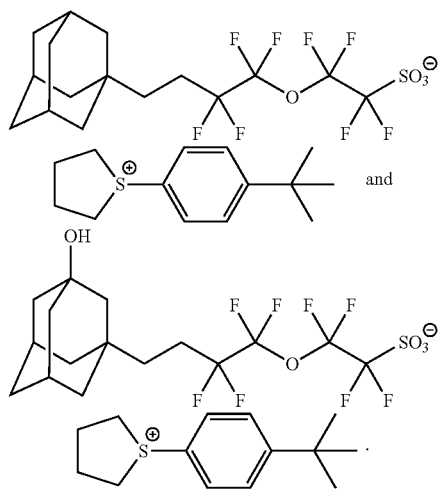

and

8. The sulfonic acid derivative compound of claim 1 selected from the group consisting of

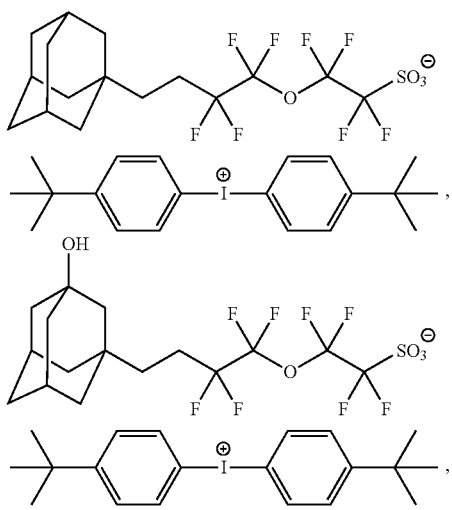

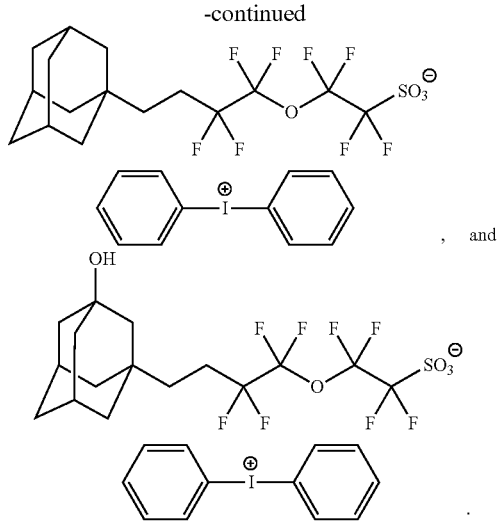

, and

9. A composition comprising:
(i) at least one photoacid generator compound represented by Formula (I):

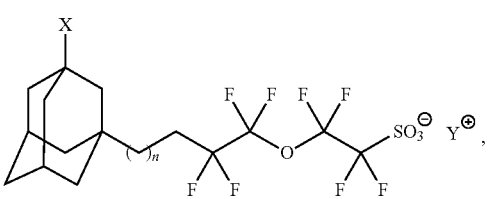 (I)

wherein
X is either H or —OH; and
Y is a cation selected from either Formula A or B:

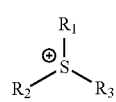 (A)

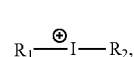 (B)

wherein
R$_1$, R$_2$, and R$_3$ are each independently selected from the group consisting of a vinyl group, an allyl group, optionally substituted (C$_1$-C$_{20}$)alkyl group, and an optionally substituted (C$_6$-C$_{15}$)aralkyl group, wherein R$_1$ and R$_2$ may be joined together along with the sulfur to which they are attached to form a ring; and
n is an integer from 1 to 10;
(ii) at least one photoresist polymer or copolymer;
(iii) an organic solvent; and, optionally,
(iv) an additive.

10. The composition of claim 9 wherein R$^1$, R$^2$, and R$^3$ are each independently an optionally substituted (C$_6$-C$_{15}$)aralkyl group; and X is H.

11. The composition of claim 9 wherein R$^1$, R$^2$, and R$^3$ are each independently an optionally substituted (C$_6$-C$_{15}$)aralkyl group; and X is —OH.

12. The composition of claim 9 wherein $R^1$ and $R^2$ are joined together along with the sulfur to which they are attached to form a ring; $R^3$ is an optionally substituted ($C_6$-$C_{15}$)aralkyl group; and X is H.

13. The composition of claim 9 wherein $R^1$ and $R^2$ are joined together along with the sulfur to which they are attached to form a ring; $R^3$ is an optionally substituted ($C_6$-$C_{15}$)aralkyl group; and X is —OH.

14. The composition of claim 9 wherein $R^1$ and $R^2$ are each independently an optionally substituted ($C_6$-$C_{15}$)aralkyl group; and X is H.

15. The composition of claim 9 wherein $R^1$ and $R^2$ are each independently an optionally substituted ($C_6$-$C_{15}$)aralkyl group; and X is —OH.

16. The composition of claim 9 wherein the photoacid generator compound is selected from the group consisting of

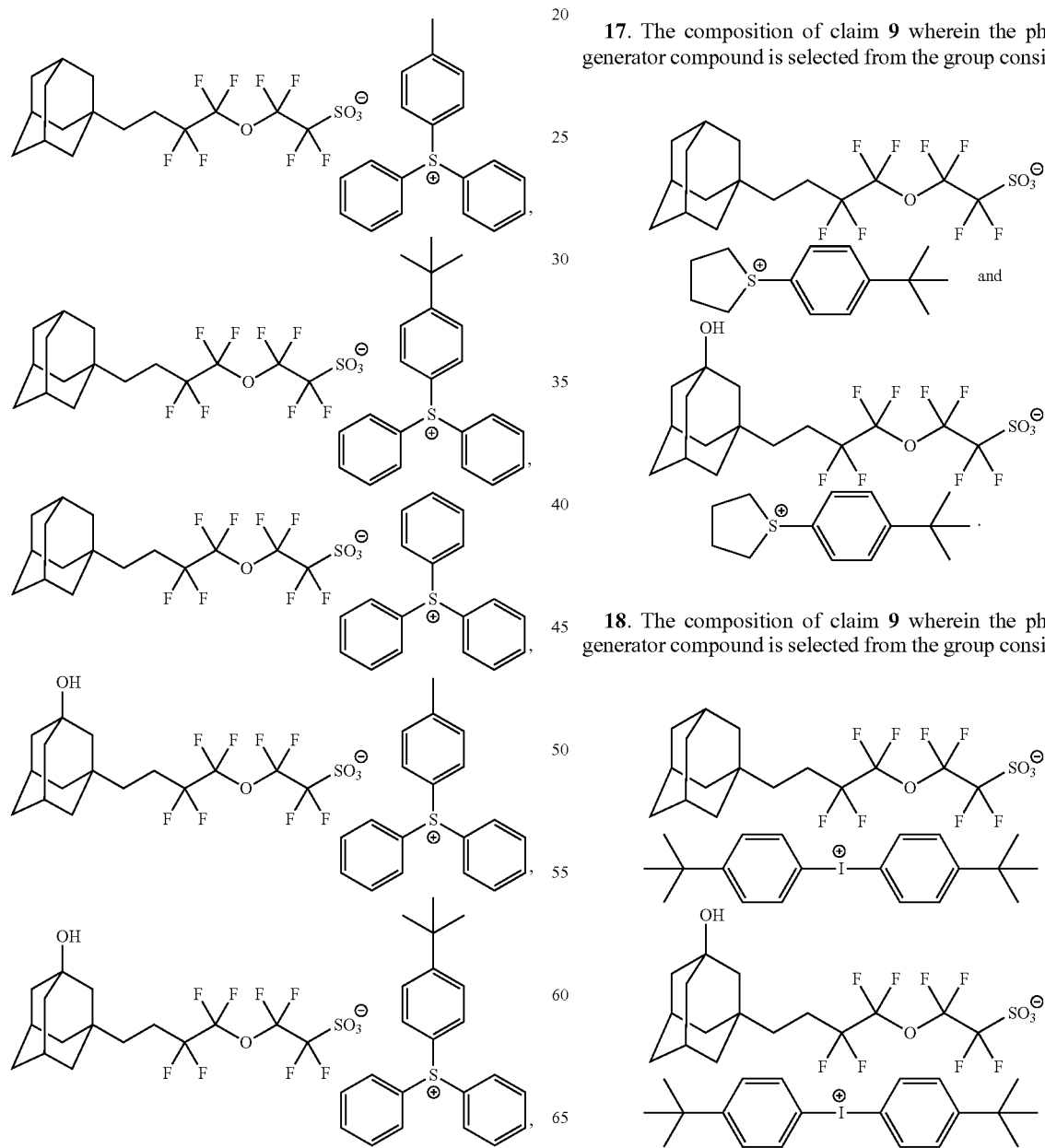

17. The composition of claim 9 wherein the photoacid generator compound is selected from the group consisting of

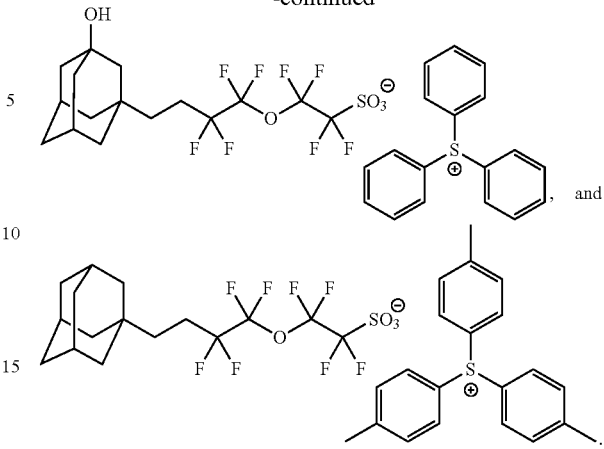

18. The composition of claim 9 wherein the photoacid generator compound is selected from the group consisting of

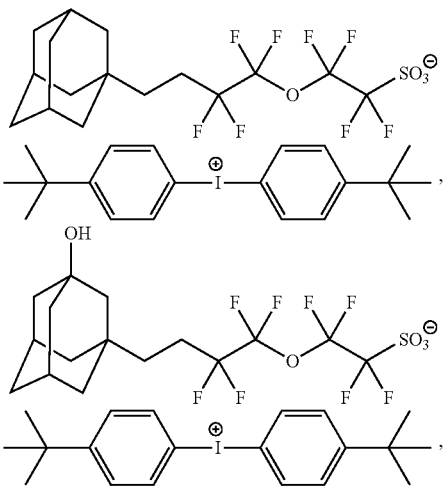

-continued

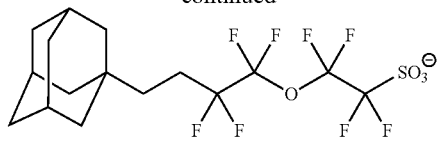

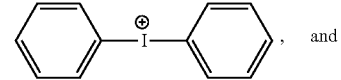

, and

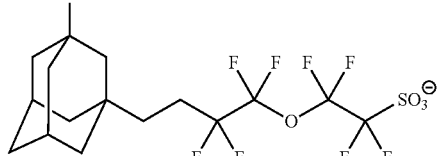

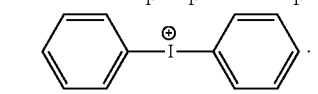

.

19. The composition of claim 9 wherein the solvent is a glycol ether selected from the group consisting of 2-methoxyethyl ether (diglyme), ethylene glycol monomethyl ether, and propylene glycol monomethyl ether.

20. The composition of claim 9 wherein the photoacid generator compound is present in the composition at from about 1 to about 10 wt. %; the at least one photoresist polymer or copolymer is present at from about 10 to about 40 wt. %; and the remainder of the composition is the organic solvent.

* * * * *